(12) United States Patent
Reeves et al.

(10) Patent No.: US 6,335,456 B1
(45) Date of Patent: Jan. 1, 2002

(54) SEMI-CONTINUOUS PROCESS FOR PREPARING BIS-SILYL CARBOXAMIDES

(75) Inventors: David Reeves, Francheville; Christophe Ruppin; Didier Faure, both of Pierre-Benite, all of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/819,950

(22) Filed: Mar. 29, 2001

(30) Foreign Application Priority Data

Mar. 29, 2000 (FR) .................................................. 00 03943

(51) Int. Cl.⁷ ....................................................... C07F 7/10
(52) U.S. Cl. .............................. 556/410; 544/69; 548/110
(58) Field of Search ............................... 556/410; 544/69; 548/110

(56) References Cited

U.S. PATENT DOCUMENTS 4,981,827 A * 1/1991 Ballard et al. ........... 556/410 X
5,082,958 A * 1/1992 Wright et al. ................. 556/410
5,142,080 A * 8/1992 Shinohara et al. ............ 556/410

FOREIGN PATENT DOCUMENTS

EP 0 021 238 A 1/1981

OTHER PUBLICATIONS

JP 63–079889—Patent Abstract of Japan, Apr. 9, 1988.
JP 63–192790—Patent Abstract of Japan, Aug. 10, 1988.

* cited by examiner

*Primary Examiner*—Paul F. Shaver
(74) *Attorney, Agent, or Firm*—Millen, White, Zelano & Branigan, P.C.

(57) ABSTRACT

For preparing bis-silyl carboxamides in a semi-continuous, reacting an amide or the N-trimethylsilyl derivative thereof with a silylating agent and, at the same time, extracting the bis-silyl carboxamide formed by distillation under reduced pressure.

17 Claims, No Drawings

SEMI-CONTINUOUS PROCESS FOR PREPARING BIS-SILYL CARBOXAMIDES

The present invention relates to a semi-continuous process for preparing bis-silyl carboxamides of formula R—C[=NSi(CH$_3$)$_3$]OSi(CH$_3$)$_3$ (I) in which R represents a linear or branched alkyl radical containing a number of carbon atoms ranging from 1 to 4; —CH=CH$_2$, —C(CH$_3$)=CH$_2$, —CH$_2$F, —CHF$_2$, —CF$_3$.

Bis-silyl carboxamides are used as agents for silylating organic compounds such as amino acids, carboxylic acids, alcohols and amides during the synthesis of pharmaceutical products or for analytical purposes.

Thus, N,O-bis trimethylsilyl)acetamide (BSA) of formula CH$_3$C[=NSi(CH$_3$)$_3$]OSi(CH$_3$)$_3$ is used in the synthesis of antibiotics such as cephalosporins.

There are many routes of access to the bis-silyl carboxamides of formula (I).

The conventional route is that which was used by Birkofer L. et al. (Angew. Chem. 1963, 75, pages 93 and 94) which consists in reacting acetamide in the presence of two equivalents of trimethylchlorosilane (TMCS) in the presence of tertiary amines as hydrochloric acid acceptors. Triethylamine is the usual solvent. This route has two major drawbacks. Firstly, the amine hydrochloride tends to sublime during the reaction and, secondly, the step of filtering off the amine hydrochloride is difficult in particular on account of the very high sensitivity of BSA to water.

French patent application FR-A-2 574 079 proposes a process for preparing BSA which consists in reacting acetic anhydride first with hexamethyldisilazane and then with trimethylchlorosilane and a tertiary amine.

Although this process produces only half as much amine hydrochloride as the process using acetamide and TMCS, it has the drawback of producing trimethylsilyl acetate as a byproduct, which is difficult to upgrade.

Processes which do not co-produce amine hydrochloride have also been proposed.

These processes involve reacting acetamide or the N-trimethylsilyl derivative thereof with trimethylsilylimidazole or alkyl or aryl derivatives thereof as disclosed in patent application JP 63-79889.

Similarly, U.S. Pat. No. 4,276,423 discloses a batchwise process for preparing BSA, which consists in placing acetamide or N-(trimethylsilyl)acetamide (mono-BSA) in contact with 1-(trimethylsilyl)imidazole (TMSIm) and then in reacting them under reduced pressure and heating them gradually to a temperature of not more than 180° C. and removing the BSA from the reaction medium during the synthesis.

The advantage of this process is that it does not co-produce amine hydrochloride.

However, in this process, it is necessary to heat the reaction medium to a sufficiently high temperature in order to displace the reaction equilibrium (A):

(A)

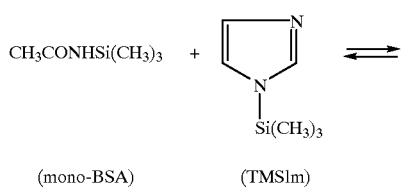

(mono-BSA)    (TMSIm)

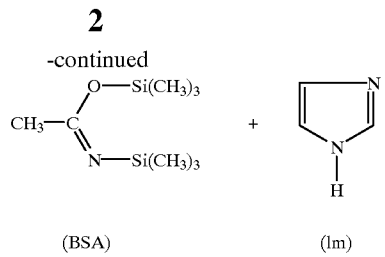

(BSA)    (Im)

towards the formation of BSA and imidazole (Im) and to extract the said BSA by distillation.

Working in this way has the drawback of involving an appreciable residence time of the BSA in the reaction medium, resulting in a partial decomposition of the BSA, this unstable product thermally decomposing into hexamethyldisiloxane and acetonitrile.

A semi-continuous process has now been found for preparing bis-silyl carboxamides of formula (I):

(1)

in which R represents a linear or branched alkyl radical containing a number of carbon atoms ranging from 1 to 4; preferably unsubstituted or fluorosubstituted alkyl, especially —CH=CH$_2$, —C(CH$_3$)=CH$_2$, —CH$_2$F, —CHF$_2$, —CF$_3$ by reacting an amide RCONH$_2$ (2) or the N-trimethylsilyl derivative thereof RCONHSi(CH$_3$)$_3$ (3) with a silylating agent R$^1$Si(CH$_3$)$_3$ (4) according to the reactions:

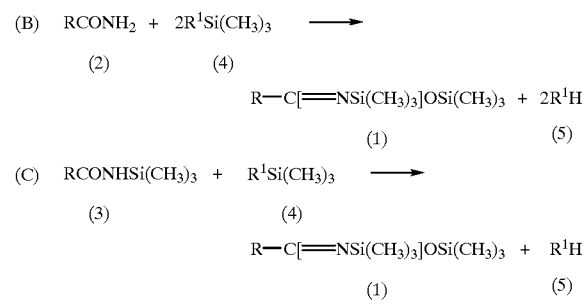

in which R$^1$ is chosen from pyrazolyl, imidazolyl, 1,2,4-triazolyl, pyrrolidinyl, morpholinyl and benzotriazolyl radicals, optionally substituted with one or more linear or branched alkyl residues containing a number of carbon atoms ranging from 1 to 4; characterized in that the following steps are simultaneously carried out:

I. continuously and gradually introducing at preferably a substantially constant flow rate the amide (2) or the N-trimethylsilylderivative thereof RCONHSi(CH$_3$)$_3$ (3), or alternatively the amide (2) or the N-trimethylsilyl derivative thereof (3) and some of the silylating agent R$^1$Si(CH$_3$)$_3$ (4) as a mixture or separately into a reactor containing a stirred distillation residue, comprising all or some of the silylating agent R$^1$Si(CH$_3$)$_3$ (4) brought to a temperature ranging from 130° C. to 190° C. and preferably between 150° C. and 180° C., and II. gradually distilling off the resultant bis-silyl carboxamide (1) as it is formed by distillation at a pressure below atmospheric pressure and preferably at a pressure of between 1×10$^3$ Pa (10 mbar) and 2×10$^4$ Pa (200 mbar).

According to the present invention, the expression "all or some" means that when the reagents (2) or (3) are irtroduced, the distillation residue comprises all of the silylating agent (4) and when the process is performed according to the variant which consists in introducing the amide (2) or the N-trimethylsilyl derivative thereof (3) and the silylating agent (4) or a mixture thereof, the distillation residue consists essentially of some of the said silylating agent (4) used, this portion representing a molar amount of not more than 40% of the total amount of (4) used. According to this variant, the introduction of the reagents is stopped when at most the working volume of the reactor is reached.

According to the present invention, the reagents introduced may be heated beforehand.

The silylating agent $R^1Si(CH_3)_3$ according to the present invention is chosen from nitrogen heterocycles containing at least one nitrogen atom bearing a hydrogen atom which may be substituted with an $—Si(CH_3)_3$ group, and optionally another hetero atom such as oxygen.

As illustrations of such compounds which may be used according to the invention, mention will be made of 1-(trimethylsilyl)imidazole and the alkyl derivatives thereof, such as 1-(trimethylsilyl)-2-methylimidazole, 1-(trimethylsilyl)-2-ethyl-4-methylimidazole, 1-trimethylsilyl-4-methylimidazole; 1-trimethylsilyl-1,2,4-triazole, 1-trimethylsilyl-pyrrolidine, 4-trimethylsilylmorpholine, 1-(trimethyl-silyl)pyrazole and the alkyl derivatives thereof such as 1-(trimethylsilyl)-3-methylpyrazole, 1-(trimethyl-silyl)-4-methylpyrazole and 1-(trimethylsilyl)benzo-1,2,3-triazole.

According to the present invention, the silylating agent will be carefully selected such that the bis-silyl derivative (1) formed is the most volatile compound.

The reagents are used in the case of reaction (B) in molar ratios (4)/(2) ranging from 2 to 4 and preferably between 2.3 and 2.7, and in the case of reaction (C), in molar ratios (4)/(3) ranging from 1 to 2 and preferably between 1.3 and 1.7.

The reactions according to the invention are carried out without using any catalyst or activator and without solvent.

The crude bis-silyl carboxamide (1) obtained according to the invention is purified by fractional distillation under reduced pressure. The distillation residue consisting mainly of the N-trimethylsilyl amide (3) may advantageously be recycled during a subsequent synthesis operation.

The process according to the present invention applies most particularly to the preparation of N,O-bis (trimethylsilyl)acetamide (BSA) from acetamide or the N-trimethylsilyl derivative thereof (mono-BSA) and 1-(trimethylsilyl)imidazole as silylating agent. In this case, R1 represents an imidazolyl radical and the heterocycle $R^1H$ co-produced is imidazole.

According to the present invention, after all of the bis-silyl carboxamide (1) has been extracted, the heterocycle $R^1H$ co-produced may be converted into silylating agent (4) by reacting it with hexamethyldisilazane (HMDZ) (6) according to the reaction:

$$2R^1H + H—N[Si(CH_3)_3]_2 \longrightarrow 2R^1Si(CH_3)_3 + NH_3 \quad (D)$$
$$(5) \qquad\qquad (6) \qquad\qquad\qquad (4)$$

The process is preferably performed using a slight excess of HMDZ relative to the stoichiometry of the reaction (D). The reaction is generally carried out at atmospheric pressure, under an inert and dry atmosphere.

The HMDZ is introduced into the reactor containing the stirred heterocycle $R^1H$ and is brought to a temperature ranging from 80° C. to 200° C. and at least to a temperature above the melting point of $R^1H$.

When the introduction of HMDZ (6) is complete, the excess HMDZ is removed and the silylating agent obtained may be used directly for a subsequent operation.

The $NH_3$ produced is advantageously absorbed in the water to give ammoniacal solutions, which may be sold.

The process according to the present invention makes it possible to work at elevated temperature without any appreciable formation of degradation products and with high production efficiency.

The examples which follow illustrate the invention.

EXAMPLE 1

Synthesis of N,O-bis(trimethylsilyl)acetamide (BSA) from N-(trimethylsilyl)acetamide (mono BSA) and 1-(TMSIm) semi-continuously at 150° C. on a 20-plates column under a reduced pressure of $1.05 \times 10^4$ Pa (105 mbar):

The reaction is carried out in a 500 ml glass round-bottomed flask equipped with a stirrer and on which is mounted a 20-theoretical-plates distillation column of Oldershaw type. The top of the column, equipped with a reflux timer, is connected to two condensers with double circulation to condense and recover the organic compounds. The outlet of the condensers is connected to a vent line comprising a cardice trap, followed by a vacuum pump. The flask is fitted with a jacketed dropping funnel, a temperature probe and an inertization system.

After purging all of the apparatus with nitrogen, 1.56 mol of 1-(trimethylsilyl)imidazole (TMSIm) (218.3 g) are introduced into the flask and heated to 150° C. under a reduced pressure of $2 \times 10^4$ Pa (200 mbar). Next, the introduction of the mono BSA from a heated dropping funnel into the flask is commenced at a flow rate such that all of the mono BSA (1 mol #131.4 g) is introduced in 260 minutes.

After about 30 minutes of introduction of the mono BSA, the pressure in the flask is reduced, gradually, to $1.05 \times 10^4$ Pa (105 mbar) and the BSA appears at the top of the column. The reflux ratio (rate of reflux/rate of removal) is between 48/2 and 68/2 and the temperature at the top of the column is from 81 to 85° C. during the removal of the BSA. Towards the end of the synthesis, the temperature of the flask is raised from 150° C. to 180° C. The reflux ratio is increased to 99/1.

The total mass of crude BSA thus obtained is 198.6 g with an average purity of 84.2%, corresponding to a molar yield of BSA of 82.2% (relative to the mono BSA used) for a conversion of mono BSA of 89.4%, resulting in a selectivity towards BSA of 92%. The production efficiency ranges between 24 and 28.2 ml/h (average 26.0 ml/h) during the removal of BSA. The cardice trap contains 0.45 g of organic compounds (including 30% acetonitrile and 67% hexamethyldisiloxane).

203.8 g remain in the reactor, consisting of a mixture of imidazole and of the excess TMSIm corresponding to a degree of recovery of imidazole of 98.9%.

EXAMPLE 2

Synthesis of N,O-bis(trimethylsilyl)acetamide (BSA) from mono BSA and TMSIm semi-continuously at 175° C. on a 20-plates column under a reduced pressure of between $2 \times 10^4$ Pa (200 mbar) and $0.95 \times 10^4$ Pa (95 mbar):

The reaction is carried out in the same apparatus as that used in Example 1, with the same contents of starting materials and the same procedure. Before introducing the mono BSA, the temperature in the flask is stabilized at 175° C. and the pressure is stabilized at 200 mbar. The pressure in the flask is gradually reduced as the mono BSA is introduced, down to $0.95 \times 10^4$ Pa, and the temperature at the top of the column is between 90° C. and 105° C. with a reflux ratio of from 58/2 to 99/1.

The molar yield of BSA is 79.6% (relative to the mono BSA introduced) with an average purity of 81.0% for an 86.2% conversion of the mono BSA. The production efficiency ranges between 26.4 and 43.2 ml/h (average 39.0 ml/h) during the removal of BSA. The cardice trap contains 0.6 g of organic compounds (including 35.1% acetonitrile and 60% hexamethyldisiloxane).

The mixture of TMSIm and imidazole which remains in the flask corresponds to a degree of recovery of imidazole of 98.5%.

EXAMPLE 3

Synthesis of BSA from mono BSA and TMSIm semi-continuously at 175° C. on a 30-plates column under a reduced pressure of between $1.95 \times 10^4$ Pa (195 mbar) and $1 \times 10^4$ Pa (100 mbar):

The reaction is carried out with the same amounts of starting materials, the same procedure and the same apparatus as that used in Examples 1 and 2, but with a 30-plates distillation column.

The molar yield of BSA is 79.3% with an average purity of 81.7% for a 90.8% conversion of mono BSA. The production efficiency ranges between 18.0 and 29.4 ml/h (average 27.0 ml/h) during the removal of BSA. The cardice trap contains 0.55 g of organic compounds (including 36.6% acetonitrile, 55.4% hexamethyldisiloxane and 7.5% mono BSA).

The mixture of TMSIm and of imidazole which remains in the flask corresponds to a degree of recovery of imidazole of 98.3%.

EXAMPLE 4
(Not in Accordance with the Invention)

Synthesis of BSA from mono BSA and TMSIm batchwise on a 20-plates column under a reduced pressure of $0.15 \times 10^4$ Pa (15 mbar):

The reaction is carried out in the same apparatus as that used in Example 1.

After purging all of the apparatus with nitrogen, 1.26 mol of TMSIm (176.4 g) and 0.668 mol of mono BSA (87.7 g) are introduced at room temperature. The system is placed under a reduced pressure of $0.15 \times 10^4$ Pa and the reaction medium is heated to 100° C.

The BSA at the top of the column is distilled off over 20 h at a reflux ratio of between 100/3 and 200/3 and a temperature of between 49° C. and 59° C. The temperature at the bottom of the column increases from 100° C. to 121° C. at the end of the removal of BSA.

The total mass of crude BSA removed is 118.9 g with an average purity of 90.8%, resulting in a molar yield of BSA of 79.5% with an 87% conversion of mono BSA. The production efficiency ranges between 6.0 and 8.4 ml/h (average 7.5 ml/h) during the removal. The cardice trap contains 5.2 g of organic compounds consisting of 20.2% acetonitrile and 79.8% hexamethyldisiloxane.

EXAMPLE 5
(Not in Accordance with the Invention)

Synthesis of BSA from mono BSA and TMSIm batchwise on a 20-plates column under a reduced pressure of $1 \times 10^4$ Pa:

The reaction is carried out in the same apparatus as that used in Example 1.

After purging all of the apparatus with nitrogen, 1.139 mol of mono BSA (149.5 g) and 1.480 mol of TMSIm (207.4 g) are introduced at room temperature. The system is placed under a reduced pressure of 100 mbar and the reaction medium is heated to 130° C.

The BSA is removed at the top of the column over 24 h at a reflux ratio of from 80/3 to 80/4. The temperature is between 78° C. and 87° C. The temperature at the bottom of the column rises from 130° C. to 162° C. at the end of the extraction of BSA.

The total mass of crude BSA removed is 154.2 g with an average purity of 84.6%. This corresponds to a molar yield of BSA of 56.3% relative to the mono BSA used. As the conversion of the mono BSA is 85.9%, the selectivity towards BSA with respect to mono BSA is thus limited to 65.5%. The production efficiency ranges between 6.0 and 15.0 ml/h (average 10 ml/h) during the removal. The cardice trap contains 19.12 g of organic compounds consisting of 22.2% acetonitrile and 77.8% hexamethyldisiloxane.

Table 1 below summarizes the conditions and results of the examples described above. This table indicates the average production efficiency, which is expressed relative to the reference production efficiency p obtained in Example 4 (batchwise process). In this Table 1: C denotes "complies with the invention"; NC denotes "does not comply with the invention".

TABLE 1

SYNTHESIS OF N, O-BIS (TRIMETHYLSILYL)ACETAMIDE (BSA)
from N-(TRIMETHYLSILYL)ACETAMIDE (MONO BSA)
and 1-(TRIMETHYLSILYL)IMIDAZOLE (TMSIm)

| Ex. No. | PROCESS | TEMPERATURE OF THE REACTION MEDIUM ° C. | MOLAR YIELD OF BSA (RELATIVE TO THE MONO BSA USED) % | SELECTIVITY TOWARDS BSA (WITH RESPECT TO THE MONO BSA) % | AVERAGE TITRE OF THE BSA EXTRACTED % | AVERAGE PRODUCTION EFFICIENCY |
|---|---|---|---|---|---|---|
| 1. (C) | Semi-continuously with introduction of mono BSA into the total amount of TMSIm under a reduced pressure of $1.05 \times 10^4$ Pa | 150 | 82.2 | 92.0 | 84.2 | 3.5 p |
| 2 (C) | As (1) but under a reduced pressure of | 175 | 79.6 | 92.3 | 81.0 | 5.2 p |

TABLE 1-continued

SYNTHESIS OF N, O-BIS (TRIMETHYLSILYL)ACETAMIDE (BSA)
from N-(TRIMETHYLSILYL)ACETAMIDE (MONO BSA)
and 1-(TRIMETHYLSILYL)IMIDAZOLE (TMSIm)

| Ex. No. | PROCESS | TEMPERATURE OF THE REACTION MEDIUM °C. | MOLAR YIELD OF BSA (RELATIVE TO THE MONO BSA USED) % | SELECTIVITY TOWARDS BSA (WITH RESPECT TO THE MONO BSA) % | AVERAGE TITRE OF THE BSA EXTRACTED % | AVERAGE PRODUCTION EFFICIENCY |
|---|---|---|---|---|---|---|
| 3 (C) | between 2.10 × 10$^4$ Pa and 0.95 × 10$^4$ Pa As (2) but under a reduced pressure of between 1.95 × 10$^4$ Pa and 1 × 10$^4$ Pa on 30 theoretical plates | 175 | 79.3 | 90.0 | 81.7 | 3..6 p |
| 4 (NC) | Batchwise under a reduced pressure of 0.15 × 10$^4$ Pa | 101→121 | 79.5 | 91.4 | 90.8 | p |
| 5 (NC) | Batchwise under a reduced pressure of 1 × 10$^4$ Pa | 129→162 | 56.3 | 65.5 | 84.6 | 1.33 p |

EXAMPLE 6

Synthesis of BSA semi-continuously on a 20-plates column with introduction of acetamide into the total amount of TMSIm at 165° C. under a reduced pressure of between 2×10$^4$ Pa and 1.55×10$^4$ Pa:

The reaction is carried out in the same apparatus as that used in Example 1, with a preheating system to pour the molten acetamide.

After purging the entire apparatus with nitrogen, 2.35 mol of TMSIm (351.1 g at 94%) are introduced into the round-bottomed flask and heated to 165° C. under reduced pressure (2×10$^4$ Pa). Next, the introduction of the molten acetamide from the heated dropping funnel into the flask is commenced at a flow rate such that all of the acetamide (0.955 mol=57 g at 98.9%) is introduced in 360 min. The pressure in the flask is gradually reduced as the acetamide is introduced, from 2×10$^4$ Pa to 1.55×10$^4$ Pa. The temperature at the top of the column is between 98° C. and 105° C. with a reflux ratio of between 98/2 and 92/8.

A total mass of crude BSA of 155.7 g is thus obtained, with an average purity of 68.6%, corresponding to a 55.0% molar yield of BSA relative to the acetamide used. The conversion of the acetamide is quantitative. The selectivity of its conversion into BSA and mono BSA is 64.8%. The production efficiency ranges between 22.2 and 27.6 ml/h (average 26.0 ml/h) during the removal of the BSA. The cardice trap contains 11.7 g of organic compounds consisting of products resulting from the degradation (51.27% by weight of HMDO, 36.6% by weight of acetonitrile) and small amounts of entrained products (mono BSA and BSA). The large amount of volatile organic compounds recovered in the trap is due essentially to the water and acetic acid present in the starting acetamide.

EXAMPLE 7
(Not in Accordance with the Invention)

Direct synthesis of BSA batchwise on a 20-plates column under a reduced pressure of 1×10$^4$ Pa:

The same apparatus and same amounts of reagents as previously.

After loading all of the TMSIm and acetamide into the reactor, the pressure is set at 1×10$^4$ Pa and the reaction mixture is heated to the boiling point of 140° C. The BSA is extracted at the top of the column over 17 h, with a reflux ratio of between 30/2 and 100/2 (the temperature at the top of the column is between 83° C. and 87° C.). The temperature at the bottom of the column rises from 140° C. up to 166° C. at the end of the removal of the BSA.

The molar yield of BSA relative to the acetamide introduced is 61.3% with an average purity of 70%. The conversion of the acetamide is quantitative, resulting in a selectivity towards BSA and mono BSA with respect to acetamide of 69.0%. The production efficiency ranges between 6 and 15.6 ml/h (average 9 ml/h) during the removal of BSA. The cardice trap contains 9.8 g of organic impurities.

EXAMPLE 8

Direct synthesis of BSA semi-continuously on a 20-plates column with introduction of an equimolar mixture of acetamide and crude undistilled TMSIm into a distillation residue of crude undistilled TMSIm at 175° C.:

The reaction is carried out in the same apparatus as that used in Example 1. After purging the entire apparatus with nitrogen, 1.272 mol of crude undistilled TMSIm (190.8 g at 93.5% containing 12.4 g of imidazole), prepared as in Example 9A, are introduced into the flask, which is heated to 175° C. under a reduced pressure of 2×10$^4$ Pa.

A mixture of 0.985 mol of acetamide (59 g at 98.5%) and 0.995 mol of crude undistilled TMSIm (149.3 g at 93.5% containing 9.7 g of imidazole) is prepared and introduced into the dropping funnel. The introduction of the mixture into the flask is commenced at a flow rate such that the total amount is introduced in 380 min. The pressure in the flask is gradually reduced to 1.05×10$^4$ Pa during the removal of the BSA, at a reflux ratio of between 90/2 and 55/2; the temperature at the top of the column is between 95° C. and 105° C.

The total mass of crude BSA removed is 199.5 g with an average purity of 83.6%, resulting in an 83.3% molar yield of BSA relative to the acetamide used. The conversion of the acetamide is quantitative with a selectivity of 95.3%. The production efficiency ranges between 26.9 and 35.7 ml/h (average 33.3 ml/h) during the removal of BSA. The cardice trap contains 2.1 g of organic impurities.

The distillation residue (195 g) consists of the excess TMSIm (40.5 g) and the imidazole formed (154.1 g). It is used in Example 9A.

EXAMPLE 9A

Synthesis of TMSIm starting with the distillation residue from Example 8 and hexamethyldisilazane:

The reaction is carried out in the same apparatus as that used in Example 1, except that the vent line is adapted to trap and meter continuously the ammonia formed.

1.36 mol of hexamethyldisilazane (219.5 g) are introduced over 2 h via a dropping funnel into the flask containing the 195 g of the distillation residue from Example 8, consisting of 2.264 mol of imidazole (154.1 g) and 0.289 mol of TMSIm (40.5 g) heated to 125° C. Towards the end of the introduction of the hexamethyldisilazane, the temperature of the reaction medium is raised to 170° C. under full reflux. Next, the excess hexamethyldisilazane is gradually extracted at the top of the column, at a reflux ratio of 18/2, by heating the bottom of the column to 180° C. In order to complete the distillation of the excess hexamethyldisilazane, the reaction medium is allowed to cool to 100° C. and the system is then placed gradually under a reduced pressure of $3.3 \times 10^4$ Pa at a reflux ratio of 98/2. The reaction medium is again heated up to a temperature of 170° C. at the top of the column, corresponding to the boiling point of the pure TMSIm. The system is then cooled under a stream of nitrogen to room temperature.

The bottom of the flask contains 342 g of crude TNSIm, with a purity of 98.1%, resulting in a 93.7% molar yield of TMSIm relative to the imidazole used. The TMSIm is used directly in Example 9B without distillation. In total, 17.7 g of ammonia are metered into the water scrubber, which corresponds to a yield of 92.0%.

EXAMPLE 9B

Direct synthesis of BSA semi-continuously with introduction of an equimolar mixture of acetamide and TMSIm recycled into a distillation residue of recycled TMSIm at about 175° C.:

The reaction is carried out in the same apparatus as that used in Example 1. After purging the entire apparatus with nitrogen, 200.15 g of recycled TMSIm prepared in Example 9A (1.40 mol) are introduced into the flask, which is heated to 163° C. under a reduced pressure of $2 \times 10^4$ Pa.

A mixture of 0.998 mol of acetamide (59.8 g at 98.5%) and 0.975 mol of recycled TMSIm prepared in Example 9A (139.4 g at 98.14%) is prepared and introduced into the dropping funnel. The introduction of the mixture into the flask is commenced at a flow rate such that the total amount is introduced in 400 min. The pressure in the flask is gradually reduced to 100 mbar during the removal of the BSA, at a reflux ratio of from 90/2 to 60/2; the temperature at the top of the column is between 90° C. and 106° C. The temperature at the bottom of the flask rises from 163° C. to 180° C. during the distillation of the BSA.

The total mass of crude BSA is 197.1 g with an average purity of 86.7%, resulting in an 84.1% molar yield of BSA relative to the acetamide used. The conversion of the acetamide is quantitative with a selectivity towards mono BSA and BSA of 96.2%. The production efficiency ranges between 26.8 and 30.5 ml/h (average 29.7 ml/h) during the removal of the BSA. The cardice trap contains only 1.61 g of organic impurities. The distillation residue contains 204.4 g, i.e. a mixture of TMSIm (55.4 g) and imidazole (149.0 g).

In a second step, the crude BSA is purified by fractional distillation under a reduced pressure of $5 \times 10^2$ Pa in a conventional manner. The mass of BSA is 167.6 g with a purity of 97%, resulting in an 80.1% molar yield of BSA relative to the acetamide used. The residue in the distillation vessel, consisting mainly of mono BSA, can be recycled into a subsequent operation.

Table 2 summarizes the conditions and results of Examples 6, 7, 8 and 9B.

This table indicates the average production efficiency, which is expressed relative to the reference production efficiency p' obtained in Example 7 (batchwise process).

In this Table 2, C denotes "complies with the invention" and NC denotes "does not comply with the invention".

TABLE 2

DIRECT SYNTHESIS OF N,O-BIS(TRIMETHYLSILYL)ACETAMIDE FROM ACETAMIDE ANP TMSIm

| Ex. No. | PROCESS | TEMPERATURE OF THE REACTION MEDIUM ° C. | MOLAR YIELD OF CRUDE BSA (RELATIVE TO THE ACETAMIDE USED) % | SELECTIVITY TOWARDS BSA AND MONO BSA (WITH RESPECT TO THE ACETAMIDE) % | AVERAGE TITRE OF THE BSA EXTRACTED % | AVERAGE PRODUCTION EFFICIENCY |
|---|---|---|---|---|---|---|
| 6 | (C) Semi-continuously with introduction of the acetamide to the total amount of TMSIm under a reduced pressure between $2 \times 10^4$ Pa and $1.55 \times 10^4$ Pa | 165 | 55.0 | 64.8 | 68.6 | 249 p' |
| 7 (NC) | Batchwise at a reduced pressure of $1 \times 10^4$ Pa | 140→166 | 61.3 | 69 | 70.0 | p' |
| 8 (C) | Semi-continuously with introduction of a stoichiometric mixture of acetamide and TMSIm to a distillation residue of TMSIm at 175° C. | 175 | 83.3 | 95.3 | 83.6 | 3.7 p' |
| 9B (C) | Semi-continuously with introduction of a stoichiometric mixture of acetamide and recycled TMSIm into a distillation residue of recycled TMSIm at 175° C. | 163→180 | 84.1 | 96.2 | 86.7 | 3.3 p' |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 00/03.943, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A semi-continuous process for preparing bis-silyl carboxamides of formula (I):

$$R-\underset{\underset{NSi(CH_3)_3}{\|}}{C}-OSi(CH_3)_3 \quad (1)$$

in which R represents a linear or branched aliphatic radical containing 1–4 carbon atoms comprising reacting at least one of an amide $RCONH_2$ (2) and the N-monotrimethylsilyl derivative thereof $RCONHSi(CH_3)_3$ (3) with a silylating agent $R^1Si(CH_3)_3$ (4) according to the reactions:

(B) $RCONH_2$ + $2R^1Si(CH_3)_3$ ⟶
    (2)        (4)
                   $R-C[=NSi(CH_3)_3]OSi(CH_3)_3$ + $2R^1H$
                                 (1)          (5)

(C) $RCONHSi(CH_3)_3$ + $R^1Si(CH_3)_3$ ⟶
    (3)           (4)
                     $R-C[=NSi(CH_3)_3]OSi(CH_3)_3$ + $R^1H$
                                 (1)       (5)

in which $R^1$ is chosen from pyrazolyl, imidazolyl, 1,2,4-triazolyl, pyrrolidinyl, morpholinyl and benzotriazolyl radicals, optionally substituted with one or more linear or branched alkyl residues containing 1–4 carbon atoms characterized in that the following steps are simultaneously carried out:
  I. continuously and gradually introducing the amide (2) or the N-trimethylsilyl derivative thereof $RCONHSi(CH_3)_3$ (3), or alternatively the amide (2) or the N-trimethylsilyl derivative thereof and some of the silylating agent $R^1Si(CH_3)_3$ (4) as a mixture or separately into a reactor containing a stirred distillation residue, comprising all or some of the silylating agent $R^1Si(CH_3)_3$ (4) brought to a temperature ranging from 130° C. to 190° C., and
  II. gradually distilling off the resultant bis-silyl carboxamide (1) as it is formed at a pressure below atmospheric pressure.

2. A process according to claim 1, wherein the amide $RCONH_2$ (2) and the silylating agent $R^1Si(CH_3)_3$ (4) are used in a molar ratio (4)/(2) ranging from 2 to 4.

3. A process according to claim 1, wherein the N-trimethylsilyl amide $RCONHSi(CH_3)_3$ (3) and the silylating agent (4) are used in a molar ratio (4)/(3) ranging from 1 to 2.

4. A process according to claim 1, wherein when the reagents (2) or (3) are introduced, the distillation residue comprises all of the silylating agent (4) used.

5. A process according to claim 1, wherein when the amide (2) or the N-trimethylsilyl derivative thereof (3) and the silylatinc agent (4) are introduced, the distillation residue comprises only a partial amount of said silylating agent (4) used.

6. A process according to claim 5, wherein the distillation residue comprises a molar amount of silylating agent (4) of not more than 40% of the molar amount of (4) used.

7. A process according to claim 1, wherein the amide (2) is acetamide or the N-trimethylsilyl derivative thereof(3) and the silylating agent (4) is 1-(trimethyl-silyl)imidazole.

8. A process according to claim 1, further comprising after distilling off the bis-silyl carboxamide (1), converting the resultant co-produced heterocycle $R^1H$ into silylating agent $R^1Si(CH_3)_3$ (4).

9. A process according to claim 8, comprising converting $R^1H$, at a temperature ranging from 80° C. to 200° C., with a molar excess of hexamethyldisilazane (6) relative to the stoichiometry of the following reaction (D):

$$2R^1H + H-N[Si(CH_3)_3]_2 \longrightarrow R^1Si(CH_3)_3 + NH_3 \quad (D)$$
  (5)         (6)                   (4)

in which $R^1$ is chosen from pyrazolyl, imidazolyl, 1,2,4-triazolyl, pyrrolidinyl, morpholinyl and benzotriazolyl radicals, optionally substituted with one or more linear or branched alkyl residues containing a number of carbon atoms ranging from 1 to 4.

10. A process according to claim 9, wherein $R^1$ represents an imidazolyl radical and $R^1H$ is imidazole.

11. A process according to claim 1, wherein the stirred distillation residue is preheated to a temperature of 130–190° C. prior to the introduction of any of (2) and (3).

12. A process according to claim 1, wherein the stirred distillation residue is preheated to a temperature of 150–180° C. prior to the introduction of any of (2) and (3).

13. A process according to claim 1, wherein the distillation is conducted at a pressure of $1 \times 10^3$ Pa to $2 \times 10^4$ Pa.

14. A process according to claim 1, wherein R represents unsubstituted alkyl or fluoro-substituted alkyl.

15. A process according to claim 1, wherein R represents $-CH=CH_2$, $-C(CH_3)=CH_2$, $-CH_2F$, $-CHF_2$ or $CF_3$.

16. A process according to claim 2, wherein the molar ratio is between 2.3 and 2.7.

17. A process according to claim 3, wherein the molar ratio is between 1.3 and 1.7.

* * * * *